(12) United States Patent
Wheeler

(10) Patent No.: US 8,292,847 B2
(45) Date of Patent: Oct. 23, 2012

(54) SYSTEMS AND METHODS FOR VACUUM-ASSISTED REGENERATION OF DAMAGED TISSUE

(75) Inventor: William K. Wheeler, Alamo, CA (US)

(73) Assignee: Raptor Ridge, LLC, Alamo, CA (US)

( * ) Notice: Subject to any disclaimer, the term of this patent is extended or adjusted under 35 U.S.C. 154(b) by 628 days.

(21) Appl. No.: 12/344,128

(22) Filed: Dec. 24, 2008

(65) Prior Publication Data

US 2009/0171288 A1 Jul. 2, 2009

Related U.S. Application Data

(60) Provisional application No. 61/018,619, filed on Jan. 2, 2008.

(51) Int. Cl.
*A61M 1/00* (2006.01)
(52) U.S. Cl. ..................... 604/119; 604/93.01
(58) Field of Classification Search .............. 514/12; 604/119, 93.01, 313–315, 318–319, 502–503, 604/509; 435/366; 602/41; 29/428; 455/41.3
See application file for complete search history.

(56) References Cited

U.S. PATENT DOCUMENTS

| 5,119,804 A * | 6/1992 | Anstadt | 601/153 |
| 6,447,443 B1 * | 9/2002 | Keogh et al. | 600/37 |
| 6,755,807 B2 | 6/2004 | Risk, Jr. et al. | |
| 2004/0243073 A1 | 12/2004 | Lockwood et al. | |
| 2005/0261189 A1 | 11/2005 | Larsen et al. | |
| 2007/0093748 A1 * | 4/2007 | Nayak et al. | 604/93.01 |

OTHER PUBLICATIONS

Lindstedt et al., "A Compare Between Myocardial Topical Negative Pressure Levels of -25 mmHg and -50 mmHg in a Porcine Model," BMC Cardiovasc. Disord., 2008; 22:8:14, 7 page total.
Lindstedt et al., "Evaluation of Continuous and Intermittent Myocardial Topical Negative Pressure," J Cardiovasc Med (Hagerstown), Aug. 2008; 9(8):813-819.
Lindstedt et al., "No Hypoperfusion is Produced in the Epicardium During Application of Myocardial Topical Negative Pressure in a Porcine Model," J. Cardiothorac. Surg., Dec. 6, 2007; 3:2:53, 7 page total.
Shake et al., "Mesenchymal Stem Cell Implantation in a Swine Myocardial Infarct Model: Engraftment and Functional Effects," Ann Thorac Surg. Jun. 2002; 73(6): 1919-1926. Retrieved from the Internet: <<http://ats.ctsnetjournals.org/cgi/reprint/73/6/1919>>.
Strauer et al., "Repair of Infarcted Myocardium by Autologous Intracoronary Mononuclear Bone Marrow Cell Transplantation in Humans," Circulation. 2002; 106(15): 1913-1918. Retrieved from the Internet: <<http://circ.ahajournals.org/cgi/reprint/106/15/1913>>.

* cited by examiner

*Primary Examiner* — Tatyana Zalukaeva
*Assistant Examiner* — Benedict L Hanrahan
(74) *Attorney, Agent, or Firm* — Wilson, Sonsini, Goodrich & Rosati

(57) ABSTRACT

A system and method for regenerating damaged or necrosed tissue. Negative or vacuum pressure is applied to a surface of the damaged tissue to stimulate the revascularization of the area and/or increased blood flow to the area, which encourages the regeneration of the damaged tissue. A negative pressure device is provided that is capable of providing a sequenced vacuum treatment regimen to damaged tissue.

13 Claims, 2 Drawing Sheets

SYSTEMS AND METHODS FOR VACUUM-ASSISTED REGENERATION OF DAMAGED TISSUE

CROSS-REFERENCE TO RELATED APPLICATIONS

This application claims the benefit of provisional application 61/018,619, filed on Jan. 2, 2008, the full disclosure of which is incorporated herein by reference.

BACKGROUND OF THE INVENTION

1. Field of the Invention

The present invention relates generally to medical devices, systems, and methods. More particularly, the present invention relates to the revascularization and regeneration of damaged tissue using negative pressure.

Damaged and necrosed tissue, such as infarcted cardiac tissue, can cause major detriment to the function of vital organs. Efforts have been made to regenerate necrosed tissue by various methods to regain at least some of the tissue's original functionality. For example, some treatment methods include the introduction of stem cells into the necrosed tissue to stimulate tissue regeneration. Stem cells may be introduced into the necrosed tissue through the walls of the blood vessels existing in the tissue or by direct injection into the tissue. Other methods include treatment of the necrosed tissue using pharmaceuticals, such as polypeptides found to stimulate proliferation of cardiac cells.

Such treatment methods are, however, complex and costly. Moreover, these treatments may rely on the health of existing blood vessels in the necrosed tissue and may not stimulate the growth of new blood vessels into the damaged areas.

For these reasons, it would be desirable to provide improved systems and methods for revascularizing and regenerating damaged tissue using negative pressure on the tissue.

2. Description of the Background Art

Cardiac tissue regeneration using polypeptides is described in Larsen et al. U.S. Patent Application Publication 2005/0261189. Cardiac tissue regeneration with stem cells is described in Shake et al., "Mesenchymal Stem Cell Implantation in a Swine Myocardial Infarct Model: Engraftment and Functional Effects". Ann Thorac Surg. 2002 June; 73(6): 1919-25, and Strauer et al., "Repair of Infarcted Myocardium by Autologous Intracoronary Mononuclear Bone Marrow Cell Transplantation in Humans". Circulation. 2002; 106: 1913-1918. Use of vacuum devices in wound healing is described in Risk, Jr. et al. U.S. Pat. No. 6,755,807 and US2004/0243073. The application of negative pressure to the myocardium to enhance microvascular blood flow is described in Lindstedt et al. (2007) J. Cardiothorac. Surg. 3:2:53; (2008) BMC Cardiovasc. Disord. 22:8:14; and (2008) Cardiovasc. Med. 1:813-9.

BRIEF SUMMARY OF THE INVENTION

The present invention provides systems and methods for revascularizing and regenerating damaged tissue using negative pressure. In one embodiment, vacuum may be applied to the surface of necrosed tissue, such as infarcted cardiac tissue, to encourage the growth of capillaries into the necrosed tissue. The capillaries may then carry stem cells circulating within the blood stream to the necrosed tissue to trigger regeneration of the tissue.

Embodiments of the present invention include a system for providing a vacuum, i.e., a negative pressure below atmospheric, preferably in the range from 10 mmHg to 200 mmHg below atmospheric pressure, to the surface of necrosed tissue for the purposes of revascularizing and regenerating the tissue. The system may include a vacuum applicator or "suction cup" with circumferential bands that are isolated from one another. Each band acts independently and may include a channel to a central hub. The central hub may include a valve that regulates which of the bands receive negative pressure. In use, the vacuum applicator or suction cup may be applied to a surface of the necrosed tissue, e.g., the infarcted region of a beating heart, and vacuum may be applied to the bands in a regulated sequence to treat the necrosed tissue.

In the first aspect, the present invention provides methods for treating tissue by applying a vacuum to a surface of the tissue to be treated under conditions that promote regeneration of the tissue. The vacuum will be below atmospheric pressure, typically being at least 20 mmHg below atmospheric pressure, usually being at least 80 mmHg below atmospheric pressure. While the vacuum may be applied to any tissue where promotion of vascular regeneration may be beneficial to regenerate the tissue, the methods are particularly useful for regenerating infarcted or otherwise damaged cardiac tissue where the vacuum is applied to the epicardium over a target region of the infarcted tissue. The vacuum may be applied to the entire surface of the region of infarcted tissue or over only a portion thereof, typically being applied to an area of the epicardium in the range from 25 $mm^2$ to 3600 $mm^2$, usually from 225 $mm^2$ to 900 $mm^2$. As described above, the pressure may be applied sequentially to a plurality of adjacent zones within the region to be treated, typically where the zones are arranged in an annular pattern, e.g., a plurality of concentric annular or circle zones of tissue. The tissue is preferably applied using a vacuum applicator or "suction cup" which is connected to a suitable vacuum source, typically by a vacuum connector line. For treating infarcted tissue, the vacuum applicator may be introduced thoracoscopically while the heart is beating, typically through an intercostal route, where the vacuum connector line may then be maintained transcutaneously and connected to an external vacuum source, such as a battery powered vacuum pump which may be worn by the patient. Thus, the vacuum may be applied to the tissue over extended periods of time, typically at least eight hours, frequently for periods up to 90 days or longer. The vacuum applicator or suction cup can also be maintained subcutaneously to treat other damaged tissues with the vacuum connector line maintained transcutaneously and connected to an external vacuum source.

The vacuum may be applied continuously over one or more treatment periods. Alternatively, the vacuum may be applied in a varying or discontinuous manner according to a variety of protocols. As described above, the vacuum may be applied to different sub-regions with the target treatment region, typically in a sequential pattern in order to promote or enhance the movement of blood and other factors which can promote tissue regeneration. Alternatively, the vacuum may be applied so that a constant or varying gradient exists, e.g., with a higher vacuum near a center or middle of the target tissue region and a lower vacuum near the periphery. A variety of other continuous, intermediate, and other protocols may also be used.

The methods of the present invention may also be advantageously combined with other therapeutic protocols. For example, for the treatment of infarcted cardiac tissue, various pharmaceutical agents and/or stem cells may be introduced to the cardiac tissue before, during, and/or after applying the vacuum to the tissue.

The present invention further includes systems for applying vacuum to a tissue surface for the purpose of enhancing the regeneration of damaged tissue. Such systems typically include a vacuum applicator, a connector for coupling the vacuum applicator to a vacuum source, and a controller for adjusting the level of vacuum applied by the vacuum applicator to the tissue. The controller will adjust the level of vacuum applied in order to promote regeneration of the damaged cardiac or other tissue. For treating cardiac tissue, the applicator will be adapted to apply the vacuum to an epicardial surface and, usually, the connector will be adapted for transcutaneous placement, typically for intercostal placement so that the patient can be connected to an external vacuum source, often a miniature pump that can be worn by the patient to allow mobility.

In an exemplary embodiment, the vacuum applicator is adapted particularly for treating infarcted cardiac tissue, where the applicator is divided into a plurality of vacuum regions that are isolated from each other. Each vacuum region will be connected independently to the vacuum source(s), and a valve on the applicator will be provided to control the connection of the vacuum regions to the vacuum source. For example, the vacuum regions may be arranged as concentric annular circles, and the valve adapted to sequentially connect the annular vacuum regions to the vacuum source(s). That way, the vacuum can be applied sequentially from the outer periphery of the applicator toward the central region in order to promote progressive blood flow from healthy peripheral tissues toward the center of the damaged tissue region. A variety of other specific vacuum region patterns could also be utilized.

Further aspects and advantages of the present invention will be apparent in view of the following detailed description of the preferred embodiments.

DETAILED DESCRIPTION OF THE INVENTION

The present invention provides a system and method for regenerating damaged or necrosed tissue. In particular, negative or vacuum pressure is applied to a surface of the damaged tissue to stimulate the in-growth of new capillaries into the tissue and/or increased blood flow to the area through existing blood vessels. In either instance, the total blood flow to the damaged area may be increased, which encourages the regeneration of the damaged tissue. For example, an increased number of stem cells carried through the improved blood flow may provide improved tissue regeneration in the damaged area. Other agents for stimulating tissue regeneration or revascularization, such as stem cells or suitable pharmaceutical agents, may be introduced into the damaged region prior or during the negative pressure treatment.

Figure 1:
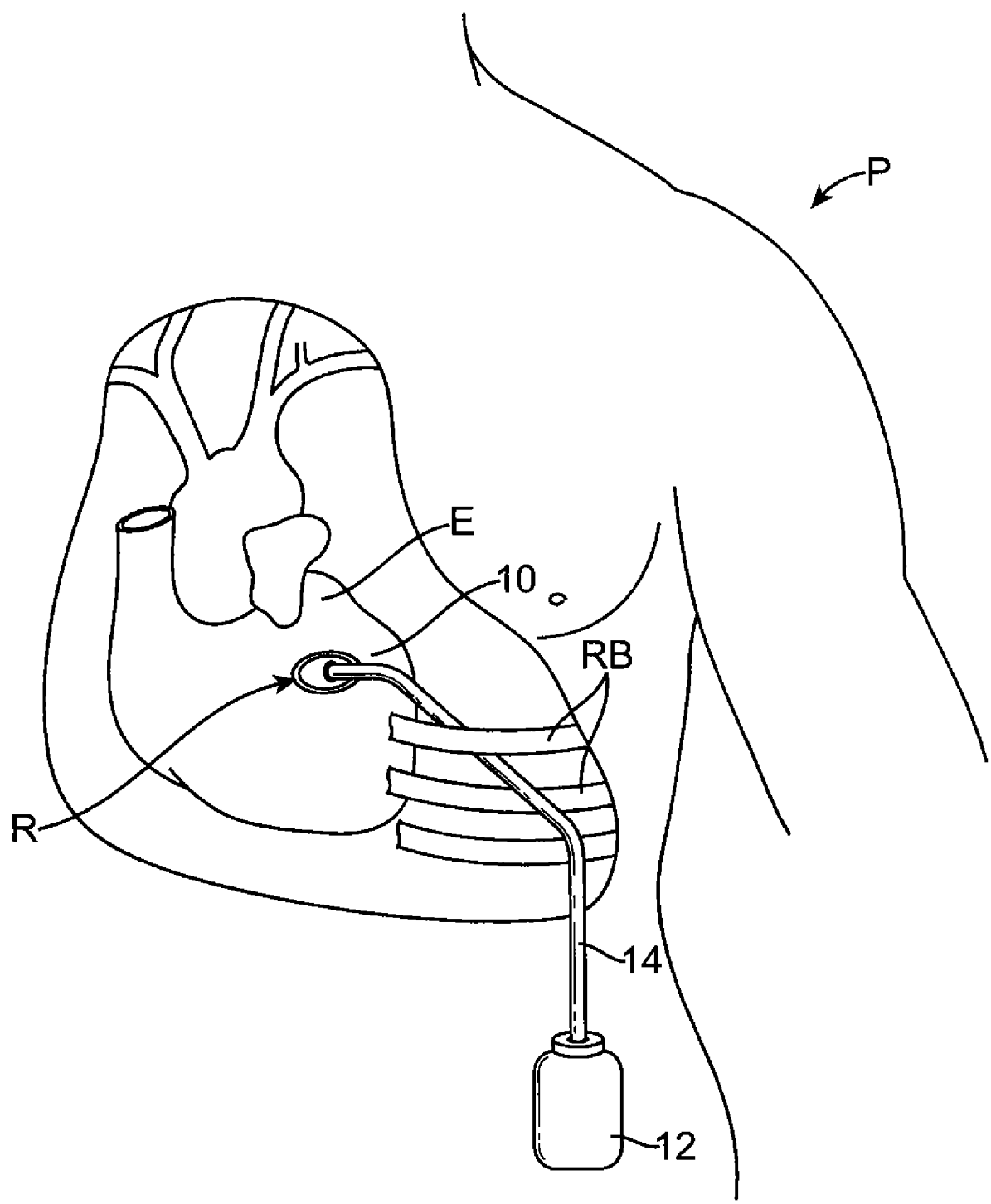
FIG. 1 illustrates a system in accordance with the principles of the present invention for connecting a vacuum applicator to the epicardium of a heart. The vacuum applicator is connected to an external vacuum source, such as a pump which is connected intercostally by a transcutaneous vacuum line.

Referring now to FIG. 1, Patient having a Region of infarcted cardiac tissue, typically following a myocardial infarction, may be treated in accordance with the principles of the present invention by engaging a vacuum applicator 10 against the Epicardium of the heart so that the applicator forms an isolated vacuum region over the epicardial tissue. The vacuum applicator 10 may be connected to a vacuum source 12, typically a small battery powered pump, which may be worn externally by the patient. The pump 12 will include control circuitry for adjusting the level of vacuum applied within the vacuum region over the Epicardium. Typically, a pressure sensor will be provided on the applicator which will feedback pressure information to the controller within the pump 12. The level of vacuum being applied to the tissue can be controlled at a fixed control point, could be regulated to variable control points, could be subject to an on-off profile, or could have a variety of adjustable vacuum zones, as discussed in more detail in connection with FIG. 2 below. The vacuum applicator 10 will usually be connected to the vacuum pump 12 by a vacuum line 14, where the vacuum line may be adapted for transcutaneous access to the vacuum applicator, allowing the patient to wear the vacuum pump 12 while the applicator 10 is maintained internally. The vacuum applicator will often be implanted thoraciscopically while the patient's heart remains beating and where the connector 14 is introduced intercostally between the ribs RB. Methods for intercostally access to a beating heart are well-described in the medical and patent literature.

Figure 2:
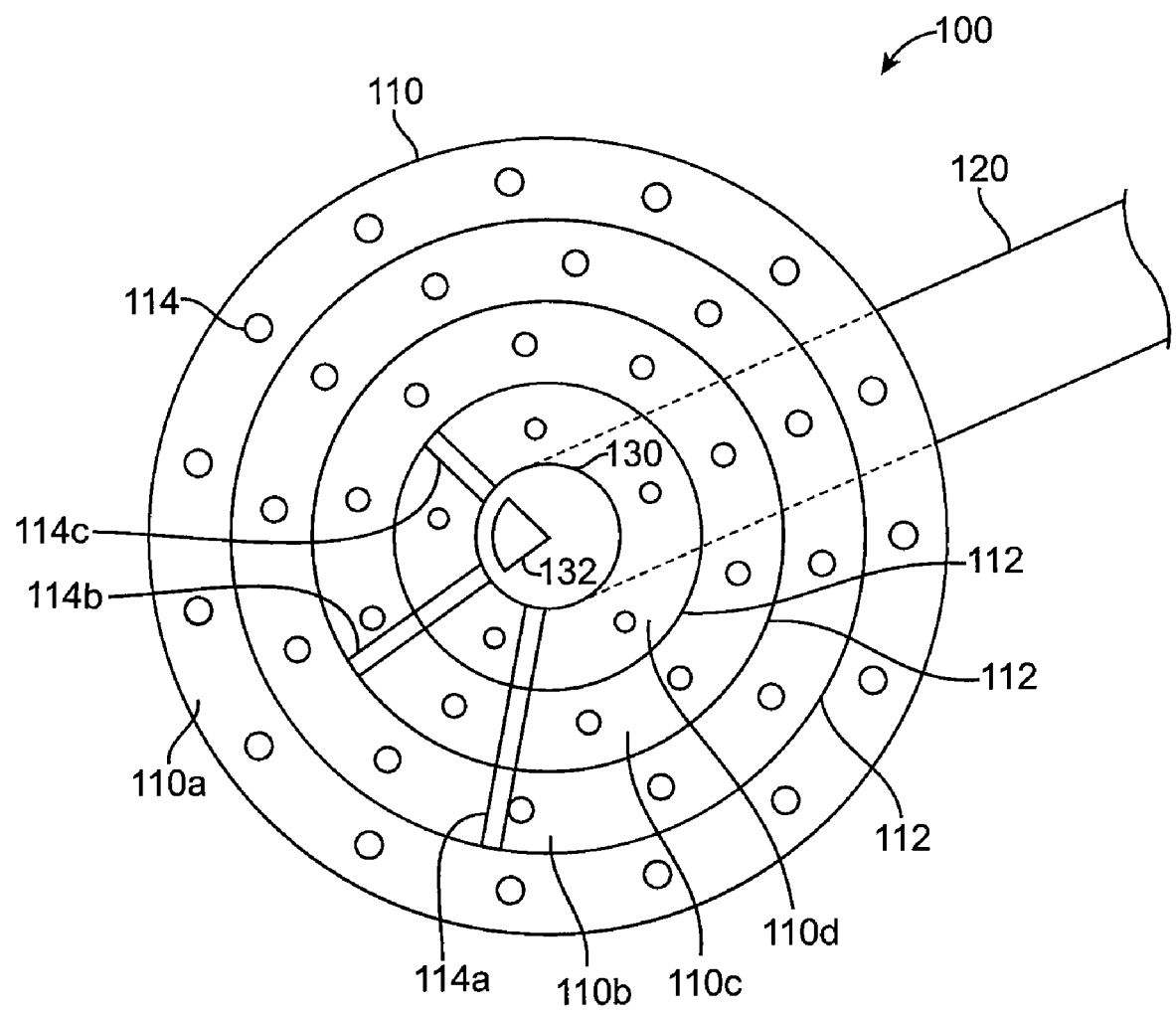
FIG. 2 shows a vacuum-assisted tissue regeneration device in accordance with an embodiment of the present invention.

Particular vacuum applicator embodiments of the present invention include a negative pressure device for performing the vacuum treatment on damaged tissue. As shown in FIG. 2, device 100 includes a suction cup 110 that includes a series of vacuum bands 110a, 110b, and 110c. Each of the vacuum bands is separated from each other using barriers 112, which enable each vacuum band to be isolated from its adjoining band and actuated independently thereof. Other arrangements may also be made to divide the face of suction cup 110 into vacuum regions, such as quadrants, etc.

In one embodiment, apertures 114 may be provided in the suction cup 110 that communicate with a rear portion of the device connected to vacuum source 120. Other arrangements may also be used to communicate the vacuum from the rear portion, such as a series of continuous channels in the face of the suction cup 110. In one embodiment, a central hub 130 may be connected with vacuum source 120. Central hub 130 may communicate with each of the vacuum bands 110a/b/c on the face of suction cup 110 via channels 114a/b/c. Hub 130 may also include a valve 132 (e.g., a rotating cam) for regulating the vacuum supplied to each of the vacuum bands by blocking or unblocking channels 114a/b/c. In one embodiment, a central portion 110d of the suction cup 110 is provided with constant vacuum not subject to the regulating valve 132 so as to maintain the position of device 100 on the tissue (e.g., maintain the device on a patient's beating heart). The material of the suction cup 110 may be of a durometer and compliance so as to allow attachment to the outside surface of a patient's tissue (e.g., to the outside of a beating heart). In some instances, this requires a highly complaint material. In some embodiments, the material of barriers 112 may be more rigid than the material used for the body of the suction cup 110, such that the barriers 112 are able to separate the vacuum bands from one another.

In use, vacuum region 110d is used to attach the suction cup 110 to the patient's damaged tissue. Valve 132 may then be used to regulate the sequence in which the vacuum bands are activated to treat the damaged tissue. For example, the vacuum bands may be activated in a given sequence as the valve 132 rotates. Some of the vacuum bands may receive constant vacuum while others may be deactivated. The vacuum provided to the damaged tissue may be pulsed or constant. The regulating valve 132 may be controlled so as to combine a number of these methods into a treatment regimen.

For example, the vacuum bands may be activated in sequence for a period of time, then certain bands may be provided with constant vacuum for a period of time, then all of the bands may be pulsed together for a period of time, etc. It should be understood that rotating valve 132 is only an illustrative embodiment of the regulating valve and its physical limitations in no way limit the extent to which the vacuum bands may be controlled. For example, valve 132 may be electronically controlled to individually regulate whether each of the vacuum bands receives negative pressure from source 120. In use, vacuum source 120 may be attached to a pump (not shown) worn outside of the body (e.g., on a harness). In the context of treating infarcted cardiac tissue, device 100 may be installed in the patient on a temporary basis through a small incision between the ribs.

While the above is a description of the preferred embodiments of the invention provided to illustrate its general concepts and not to limit the scope of the invention. Various alternatives, modifications, and equivalents may be used within the spirit of the invention.

What is claimed is:

1. A method for treating necrosed tissue, said method comprising:
    applying a vacuum to a surface of the necrosed tissue under conditions that promote regeneration of the tissue, wherein the vacuum is applied for a time period of at least 8 hours;
    wherein the tissue comprises infarcted cardiac tissue;
    wherein the vacuum is applied to the epicardium over a target region of infarcted tissue; and
    wherein the vacuum is applied in a gradient with a higher vacuum near a middle of a target region and a lower vacuum is applied near a periphery of the target region.

2. A method as in claim 1, wherein the vacuum is at least 10 mmHg.

3. A method as in claim 1, wherein the vacuum is applied over an area of the epicardium in the range from 25 mm$^2$ to 3600 mm$^2$.

4. A method as in claim 1, wherein the pressure is applied sequentially to a plurality of adjacent zones.

5. A method as in claim 4, wherein at least some of the zones are arranged annularly.

6. A method as in claim 1, further comprising positioning a vacuum cup on the tissue surface and coupling a vacuum source to the vacuum cup.

7. A method as in claim 6, wherein the tissue is internal and the vacuum cup is disposed subcutaneously.

8. A method as in claim 7, wherein the vacuum source is disposed subcutaneously.

9. A method as in claim 7, wherein the vacuum source is disposed externally and coupled to the vacuum cup by a transcutaneous connecting line.

10. A method as in claim 1, wherein the vacuum is applied continuously over a period in the range from 8 hours to 90 days.

11. A method as in claim 1, wherein the vacuum is applied intermittently over a period in the range from 8 hours to 90 days.

12. A method as in claim 11, wherein the vacuum is applied over intervals in the range from 5 minutes to 60 minutes during the intermittent period.

13. A method as in claim 1, further comprising delivering pharmaceutical agents and/or stem cells to the tissue before, during, and/or after applying the vacuum.

\* \* \* \* \*